US010070838B2

(12) United States Patent
Ohishi (10) Patent No.: US 10,070,838 B2
(45) Date of Patent: Sep. 11, 2018

(54) X-RAY DIAGNOSTIC APPARATUS (71) Applicant: Toshiba Medical Systems Corporation, Otawara-shi (JP)

(72) Inventor: Satoru Ohishi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 234 days.

(21) Appl. No.: 14/953,208

(22) Filed: Nov. 27, 2015

(65) Prior Publication Data

US 2016/0151034 A1 Jun. 2, 2016

(30) Foreign Application Priority Data

Nov. 28, 2014 (JP) .................................. 2014-241736

(51) Int. Cl.
G06K 9/00 (2006.01)
A61B 6/00 (2006.01)

(52) U.S. Cl.
CPC ............ *A61B 6/504* (2013.01); *A61B 6/4266* (2013.01); *A61B 6/4441* (2013.01); *A61B 6/466* (2013.01); *A61B 6/469* (2013.01); *A61B 6/481* (2013.01); *A61B 6/487* (2013.01); *A61B 6/507* (2013.01); *A61B 6/5217* (2013.01); *A61B 6/5223* (2013.01)

(58) Field of Classification Search
None
See application file for complete search history.

(56) References Cited

U.S. PATENT DOCUMENTS

| 7,412,023 | B2 | 8/2008 | Ohishi et al. | |
| 2012/0300903 | A1* | 11/2012 | Yao | A61B 6/12 378/62 |
| 2013/0010917 | A1* | 1/2013 | Thibault | G06T 11/006 378/4 |
| 2013/0010924 | A1* | 1/2013 | Ohishi | A61B 6/022 378/42 |

FOREIGN PATENT DOCUMENTS

JP 2007-229473 9/2007

* cited by examiner

*Primary Examiner* — Sean Conner
(74) *Attorney, Agent, or Firm* — Oblon, McClelland, Maier & Neustadt, L.L.P.

(57) ABSTRACT

An obtaining unit obtains, with respect to a plurality of groups of time-course fluoroscopic images that are obtained by acquiring a subject, in at least two directions, each of which intersect, first transition information that indicates transition of a signal intensity of a contrast media in a proximal region to which the contrast media flows earlier than a region of interest. A three dimensional reconstruction unit reconstructs three-dimensional image data in the region of interest such that a value that is obtained by projecting a voxel value approximates a value of a corresponding pixel in each of the groups of time-course fluoroscopic images, the voxel value being represented by second transition information that is obtained by deforming the first transition information with a factor that is related to the contrast media. A display displays the fluoroscopic image with a blood vessel image based on the three-dimensional image data.

10 Claims, 7 Drawing Sheets

GENERATE EACH BLOOD
VESSEL IMAGE THAT IS
PROJECTED FROM POSITION
OF EACH ARM AND
SUPERIMPOSE IT ON
FIUOROSCOPIC IMAGE

X-RAY DIAGNOSTIC APPARATUS

CROSS-REFERENCE TO RELATED APPLICATIONS

This application is based upon and claims the benefit of priority from Japanese Patent Application No. 2014-241736, filed on Nov. 28, 2014; the entire contents of which are incorporated herein by reference.

FIELD

Embodiments described herein relate generally to an X-ray diagnostic apparatus.

BACKGROUND

Conventionally, for intervention or angiographic examination, a catheter is inserted through a blood vessel during fluoroscopy of an X-ray image and is moved to a site that has diseases in the heart, brain, liver, or the like. Here, on X-ray images, a blood vessel is visible for a short time only when a contrast media, or the like, is injected so that the structure of the blood vessels become visible to determine relationship between catheter and blood vessels; however, the amount of used contrast media needs to be reduced to prevent the subject from renal impairment.

For example, as the technology for reducing the amount of used contrast media, two-dimensional roadmap function which superimposes a real-time catheter image and pre-acquired blood vessel image is frequently used. Catheter image is created by subtracting pre-acquired fluoroscopic image from real-time fluoroscopic image, and then catheter moved from previous position on pre-acquired fluoroscopic image is enhanced. Blood vessel image is also created by subtracting acquisition image after contrast injection from acquisition image before contrast injection. The two-dimensional roadmap function makes it possible to understand relationship between blood vessels and catheter without using the contrast media and therefore, for example, it is used when a catheter is inserted through a complicated blood vessel, or the like. Here, in a case where the catheter is inserted through a complicated blood vessel, if a two-dimensional roadmap image is used, where a two-dimensional blood vessel image is superimposed on real-time a fluoroscopic image, there is a limitation on understanding of the three-dimensional structure of a blood vessel, and the catheter is sometimes not inserted into the target blood vessel for certain time period.

In such a case, by using a three-dimensional roadmap image where a blood vessel image that is generated from three-dimensional image data with volume-rendering processing is superimposed on a real-time fluoroscopic image, the blood vessel image for three-dimensional roadmap has more detail information than that for two-dimensional roadmap. Moreover, the orientation of the blood vessel image could be changed flexibly and easily so as to see the structure of the blood vessel clearly. However, according to the above-described conventional technology, acquisition of image data for generating a three-dimensional roadmap image is sometimes time-consuming.

DETAILED DESCRIPTION

According to an embodiment, an X-ray diagnostic apparatus includes processing circuitry and a display. The processing circuitry is configured to obtain, with respect to a plurality of groups of time-course fluoroscopic images that are obtained by acquiring a subject injected with a contrast media, in at least two directions, each of which intersect, first transition information that indicates transition of a signal intensity of the contrast media in a proximal region to which the contrast media flows earlier than a region of interest. The processing circuitry is configured to reconstruct three-dimensional image data in the region of interest such that a value that is obtained by projecting a voxel value approximates a value of a corresponding pixel in each of the groups of time-course fluoroscopic images, the voxel value being represented by second transition information that is obtained by deforming the first transition information with a factor that is related to the contrast media. The display is configured to display the fluoroscopic image with a blood vessel image based on the three-dimensional image data.

An X-ray diagnostic apparatus according to an embodiment is explained below with reference to the attached drawings. Here, the X-ray diagnostic apparatus according to the present application is not limited to the embodiment that is described below.

First Embodiment

Figure 1:
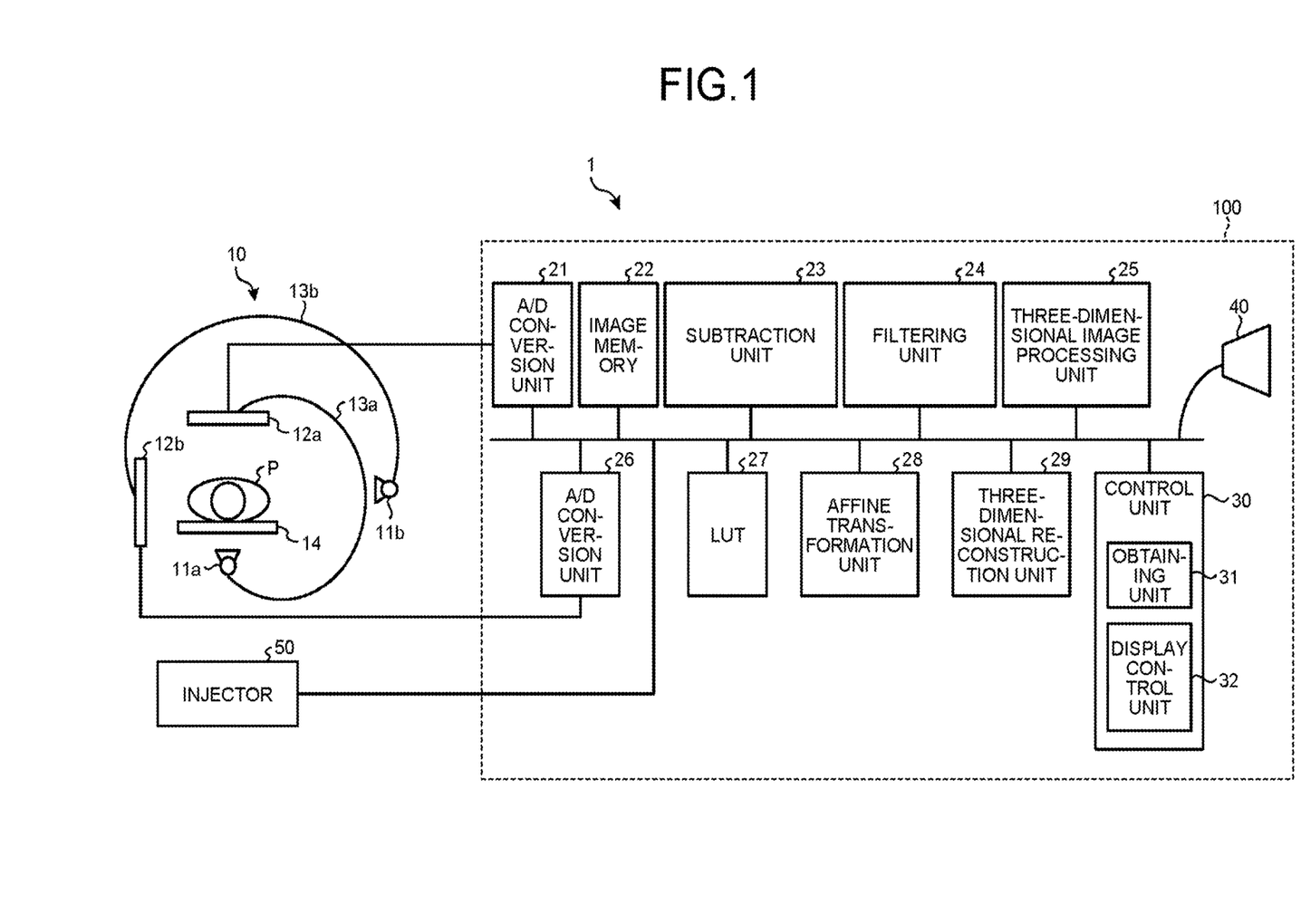
FIG. 1 is a diagram that illustrates an example of the configuration of an X-ray diagnostic apparatus according to a first embodiment.

FIG. 1 is a diagram that illustrates an example of the configuration of an X-ray diagnostic apparatus 1 according to a first embodiment. As illustrated in FIG. 1, the X-ray diagnostic apparatus 1 according to the first embodiment includes an X-ray acquisition mechanism 10 and an image processing apparatus 100. The X-ray acquisition mechanism 10 is a bi-plane acquisition mechanism that includes a first acquisition mechanism that has an X-ray tube 11a, a detector (flat panel detector (FPD), or the like) 12a, and a C-arm 13a and that includes a second acquisition mechanism that has an X-ray tube 11b, a detector (FPD, or the like) 12b, and a Ω-arm 13b. Furthermore, the X-ray acquisition mechanism 10 includes a bed 14, and it is connected to an injector 50.

The injector 50 is a device for injecting a contrast media through the catheter that is inserted into a subject P. Here, there may be cases in which injection of the contrast media from the injector 50 is started in accordance with an injection start command that is received via the image processing apparatus 100 that is described later or in accordance with an injection start command that is directly input to the injector 50 by an operator.

The C-arm 13a supports the X-ray tube 11a and the detector 12a, and it is rotated by a motor that is provided on a supporter (not illustrated) at high speed like a propeller around the subject P that lies on the bed 14. Here, the C-arm 13a is supported such that it is rotatable with regard to the XYZ axes that are the three axes that run at right angles, and it is individually rotated by an undepicted driver with respect to each axis. The Ω-arm 13b supports the X-ray tube 11b and the detector 12b, and it is rotated by a motor that is provided on a supporter (not illustrated), which is a ceiling rail, around the subject P that lies on the bed 14. Here, the Ω-arm 13b is supported such that it is rotatable with regard to the XYZ axes that are the three axes that run at right angles, and it is individually rotated by an undepicted driver with respect to each axis.

The X-ray acquisition mechanism 10 is controlled by an undepicted acquiring control unit. For example, under the control of a control unit 30 that is described later, the acquiring control unit controls various operations related to acquiring by the X-ray acquisition mechanism 10. For example, the acquiring control unit controls rotational acquiring for acquiring projection data at a predetermined frame rate while the C-arm 13a and the Ω-arm 13b are rotated. For instance, the acquiring control unit controls multiple rotational acquiring after a single contrast media is injected by using, as a trigger, the signal that is output when the injection of the contrast media from the injector 50 is started. Furthermore, while the C-arm 13a and the Ω-arm 13b are controlled so as to rotate, the acquiring control unit controls an undepicted high-voltage generator so as to cause the X-ray tube 11a or the X-ray tube 11b to generate X-rays continuously or intermittently and controls the detector 12a or the detector 12b so as to detect X-rays that are transmitted through the subject P.

As illustrated in FIG. 1, the image processing apparatus 100 includes an analog/digital (A/D) conversion unit 21, an image memory 22, a subtraction unit 23, a filtering unit 24, a three-dimensional image processing unit 25, an A/D conversion unit 26, a look up table (LUT) 27, an affine transformation unit 28, a three-dimensional reconstruction unit 29, the control unit 30, and a display unit 40. Furthermore, although not illustrated, the image processing apparatus 100 includes an input unit, such as a mouse, keyboard, trackball, or pointing device, to receive various operations from an operator in relation to the X-ray diagnostic apparatus 1.

The display 40 displays various images that are processed by the image processing apparatus 100 and various types of information, such as a graphical user interface (GUI). For example, the display 40 is a cathode ray tube (CRT) monitor or a liquid crystal monitor. The A/D conversion unit 21 is connected to the detector 12a, and it converts an analog signal input from the detector 12a into a digital signal and stores the converted digital signal as an X-ray collection image in the image memory 22. The A/D conversion unit 26 is connected to the detector 12b, and it converts an analog signal input from the detector 12b into a digital signal and stores the converted digital signal as an X-ray acquisition image in the image memory 22.

The image memory 22 stores X-ray acquisition images (projection data). For example, the image memory 22 stores projection data that is acquired by the first acquisition mechanism and projection data that is acquired by the second acquisition mechanism. Furthermore, the image memory 22 stores reconstruction data (volume data) that is reconstructed by the three-dimensional reconstruction unit 29 that is described later and three-dimensional images that are generated by the three-dimensional image processing unit 25. Furthermore, the image memory 22 stores subtraction images that are generated by the subtraction unit 23 that is described later.

The subtraction unit 23 generates subtraction images, such as digital subtraction angiography (DSA) images. For example, the subtraction unit 23 generates DSA images or blood-vessel volume data by using projection data on a mask image and a contrast image that are stored in the image memory 22 or using volume data. The filtering unit 24 performs a high-frequency accentuation filtering, or the like. The LUT 27 performs a tone conversion. The affine transformation unit 28 enlarges, minifies, moves, or the like, images.

The three-dimensional reconstruction unit 29 reconstructs reconstruction data (hereafter, referred to as the three-dimensional image data or volume data) from projection data that is acquired during rotational acquiring by the X-ray acquisition mechanism 10. For example, the three-dimensional reconstruction unit 29 reconstructs volume data from post-subtraction projection data that is stored in the image memory 22 after the subtraction unit 23 performs a subtraction on the mask image and the contrast image. Alternatively, the three-dimensional reconstruction unit 29 reconstructs volume data from the projection data that is stored in the image memory 22 after the A/D conversion unit 21 or the A/D conversion unit 26 performs a digital data conversion. Then, the three-dimensional reconstruction unit 29 stores the reconstructed volume data in the image memory 22.

Here, the three-dimensional reconstruction unit 29 receives the subtraction image that is generated by the subtraction unit 23 on the basis of the projection data that is acquired by the first acquisition mechanism. The three-dimensional reconstruction unit 29 also receives the subtraction image that is generated by the subtraction unit 23 on the basis of the projection data that is acquired by the second acquisition mechanism. Furthermore, the three-dimensional reconstruction unit 29 reconstructs volume data by using the two subtraction images. Specifically, the three-dimensional reconstruction unit 29 reconstructs volume data by using two-dimensional X-ray images that are acquired in two directions. Furthermore, generation of the above-described volume data is described later.

The three-dimensional image processing unit 25 generates a three-dimensional image from the volume data that is stored in the image memory 22. For example, the three-dimensional image processing unit 25 generates a volume rendering image or a Multi Planar Reconstruction (MPR) image from volume data. Then, the three-dimensional image processing unit 25 stores the generated three-dimensional image in the image memory 22.

The control unit 30 performs the overall control of the X-ray diagnostic apparatus 1. Specifically, the control unit 30 controls various operations related to acquiring of X-ray images by the X-ray acquisition mechanism 10, reconstruction of images, generation of displayed images, presentation of images displayed on the display unit 40, or the like. For example, the control unit 30 performs a control on acquiring of X-ray images by the first acquisition mechanism and the second acquisition mechanism. Furthermore, the control unit 30 performs a control on reconstruction of volume data from acquired projection data. Moreover, the control unit 30 performs a control on display, on the display unit 40, of a three-dimensional roadmap image where a three-dimensional image, which is generated from the reconstructed volume data, is superimposed on a fluoroscopic image. Here, as illustrated in FIG. 1, the control unit 30 includes, for example, an obtaining unit 31 and a display control unit 32.

As described above, with conventional X-ray diagnostic apparatus, as acquisition of image data for generating a three-dimensional roadmap image is time-consuming, three-dimensional roadmap images are not used as a tool for inserting a catheter. For example, in some cases, the catheter cannot be inserted into the target blood vessel during intervention or angiographic examination if the vascular structure is peculiar, if the origin of a blood vessel is narrowed, if the origin of a blood vessel is calcified, or the like.

In such a case, according to conventional technologies, for example, a two-dimensional roadmap image is generated to observe a blood vessel so that the angle for a surgery is changed. However, in the case of this method, a blood vessel is not always extracted in the appropriate direction on the generated two-dimensional roadmap image, and there is a possibility of repetition of generation of two-dimensional roadmap images and of changes in the angle. Here, if three-dimensional roadmap images can be used, the structure of a blood vessel may be understood in detail; however, as described above, as acquisition of image data for generating three-dimensional roadmap images is time-consuming, it is hard to use.

For example, if a three-dimensional roadmap image is generated in a case where a catheter cannot be inserted into the target blood vessel, the image data for reconstructing volume data is first acquired. In a case of bi-plane X-ray diagnostic apparatus, the bi-plane is first switched to a single plane, one of the arms is retracted, and the position of the subject is determined. Then, the injector is prepared, and it is ensured that the high-speed rotating arm is prevented from interfering with the subject. Afterward, the image data for reconstructing volume data is acquired and, after acquiring is completed, the injector is removed, the state of the subject is checked, and the retracted arm is returned to the original state. The above-described operation takes about at least five minutes and, if a three-dimensional roadmap image is afterward generated and displayed and then an observation is conducted, the time it takes is beyond calculation. Furthermore, if image data is acquired to generate a three-dimensional roadmap image, the radiation dose is increased, and the contrast media is further injected. Therefore, three-dimensional roadmap images are not actually used for inserting a catheter.

As different tools from the above-described three-dimensional roadmap images, for example, there are possible technologies for displaying stereoscopic images by using parallax images that are acquired while a C-shaped arm is alternately rotated to right and left or by using parallax images that are acquired by using a stereo tube. However, if parallax images are acquired while a C-shaped arm is alternately rotated to right and left, the time phases of parallax images during acquisition are different, and therefore it is sometimes difficult to obtain a stereoscopic view. For example, if the catheter is moved among the acquired parallax images, it is difficult to obtain a stereoscopic view. Furthermore, if a stereo tube is used, there is a limitation on the usable apparatus. Furthermore, if the angle with which the arm is moved when image data for reconstructing volume data is acquired is set to, for example, 200 degrees to 120 degrees, one of the arms of the bi-plane does not need to be retracted; however, it is difficult to shorten other operations.

Therefore, the X-ray diagnostic apparatus 1 according to the present application makes it possible to easily reconstruct volume data by using the image data that is captured by the bi-plane in two directions. That is, the X-ray diagnostic apparatus 1 allows reconstruction of volume data by using an acquiring program that is used for diagnosis or observation instead of a three-dimensional dedicated program; thus, when the catheter is inserted, or the like, three-dimensional roadmap images are available, and the structure of blood vessels may be understood in more detail.

Specifically, with respect to multiple groups of time-course X-ray images that are obtained by acquiring the subject, into which the contrast media has been injected, in at least two directions, the obtaining unit 31 obtains the value of a pixel that is included in the region of interest and the first transition information that indicates the transition of the signal intensity of the contrast media in the region to which the contrast media flows earlier than the region of interest. The three-dimensional reconstruction unit 29 reconstructs volume data such that the value that is obtained by projecting the voxel value, which is represented by the second transition information that is obtained by deforming the first transition information with the factor that is related to the contrast media, approximates the value of a corresponding pixel in each of the groups of the time-course X-ray images.

Here, the three-dimensional reconstruction unit 29 reconstructs three-dimensional image data such that the value that is obtained by projecting the voxel value approximates the pixel value, the voxel value being represented by the second transition information that is changed with at least one factor among dilution and spread of the contrast media within a blood vessel, speed degradation due to the friction of a blood vessel wall, and the reaching delay time. That is, the three-dimensional reconstruction unit 29 performs iterative reconstruction by using, as a priori conditions, at least one factor among dilution and spread of the contrast media, speed degradation due to the friction of a blood vessel wall, and the reaching delay time, thereby reconstructing volume data from the image data in two directions.

Figure 2:
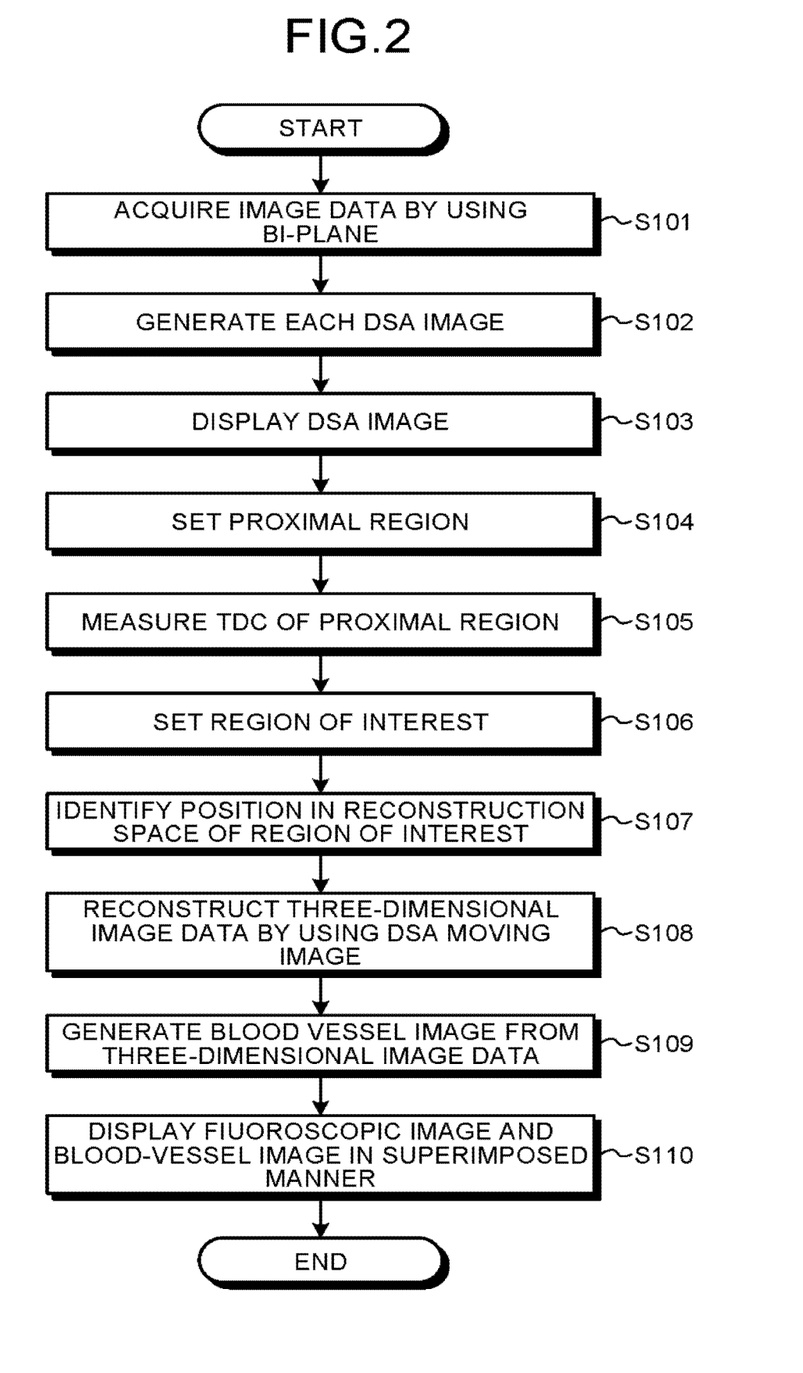
FIG. 2 is a flowchart that illustrates an example of the steps of the operation that is performed by the X-ray diagnostic apparatus according to the first embodiment.

With reference to FIG. 2, an explanation is given below of an example of the operation that is performed by the X-ray diagnostic apparatus 1 according to the present embodiment. FIG. 2 is a flowchart that illustrates an example of the steps of the operation that is performed by the X-ray diagnostic apparatus 1 according to the first embodiment. As illustrated in FIG. 2, in the X-ray diagnostic apparatus 1, under the control of the control unit 30, the X-ray acquisition mechanism 10 acquires image data by using the bi-plane (Step S101). For example, in the X-ray diagnostic apparatus 1, each of the first acquisition mechanism and the second acquisition mechanism first acquires a mask image before the contrast media is injected. Here, there may be a case where the mask image is simultaneously acquired by the first acquisition mechanism and the second acquisition mechanism or a case where it is acquired by one at a time.

After a mask image is acquired, the injector 50 injects the contrast media into the subject. Here, injection of the contrast media may be automatically started by the injector 50; however, the information that notifies the contrast media injection timing may be displayed on the display unit 40 so that an operator starts it manually (syringe) based on the information. There may be a case where it is determined whether the injector 50 is used on the basis of the thickness of a blood vessel. Furthermore, according to the present application, as the region that needs to be visualized by using the contrast media is limited (for example, only the region where a blood vessel is bifurcated), it takes a shorter time to inject the contrast media, compared to typical three-dimensional acquiring, for example, it is a shorter time by about 1 sec than the injection time during typical three-dimensional acquiring.

After the contrast media is injected into the subject, each of the first acquisition mechanism and the second acquisition mechanism acquires a contrast image. Here, a contrast image is acquired in the same manner as a mask image. That is, if the first acquisition mechanism and the second acquisition mechanism simultaneously acquire a mask image, the first acquisition mechanism and the second acquisition mechanism also simultaneously acquire a contrast image. Conversely, if the first acquisition mechanism and the second acquisition mechanism acquire a mask image one by one, they also acquire a contrast image one by one. For the above-described acquisition of a contrast image, the acquisition rate may be changed depending on, for example, the speed of a blood flow. For example, acquisition is normally conducted at the acquisition rate of 15 pair per second (pps), and there may be cases where, in the case of a blood vessel with an extremely rapid blood flow, it is changed to 30 pps or 60 pps and, in the case of a blood vessel with an extremely slow blood flow, it is changed to 6 pps or 10 pps.

As described above, after the first acquisition mechanism and the second acquisition mechanism acquire a mask image and a contrast image, the subtraction unit 23 generates each DSA image (Step S102). For example, the subtraction unit 23 subtracts the contrast image and the mask image that are acquired by the first acquisition mechanism with the course of time to generate a time-course DSA image. In the same manner, the subtraction unit 23 subtracts the contrast image and the mask image that are acquired by the second acquisition mechanism with the course of time to generate a time-course DSA image.

After the subtraction unit 23 generates the DSA images, the display control unit 32 displays each of the generated DSA images on the display unit 40 (Step S103). An operator sees each of the bi-plane DSA images that are displayed on the display unit 40 and designates the region of interest and the proximal region via the input unit. Here, the region of interest is the region of which volume data needs to be generated (e.g., the region where a blood vessel is bifurcated), and the proximal region is the blood vessel region to which the contrast media flows earlier than the region of interest (the region of a blood vessel that is closer to the heart than a blood vessel in the region of interest).

Here, the proximal region may be a single pixel; however, it is preferably the region that includes multiple pixels in order to reduce the effect of noises, and it is preferably the region where a blood vessel runs at right angle to the travelling direction of an X-ray. For example, of a blood vessel that runs at right angle to the travelling direction of an X-ray as much as possible, a line that is perpendicular to the running direction of the blood vessel or a region on the blood vessel is designated as the proximal region.

As described above, after the proximal region is designated, the obtaining unit 31 sets, as the proximal region, the position (coordinates) that is designated on the DSA image (Step S104) and measures the TDC of the proximal region (Step S105). For example, the obtaining unit 31 measures each of the TDCs of the pixels included in the proximal region by using the time-course DSA image and averages the measured TDCs to calculate the TDC of the proximal region. Here, the obtaining unit 31 interpolates the discrete value that is acquired from each of the pixels of the time-course DSA image by using a linear or high-dimensional function to calculate a continuous TDC "g(t)" of the proximal region. Furthermore, the obtaining unit 31 measures the blood vessel diameter (mm) of the proximal region and further calculates the blood vessel diameter (mm) "L" in a reconstruction space where it is assumed that the blood vessel is located substantially in the rotation center. Here, the TDC "f(t)" of the proximal region in the reconstruction space is calculated by using the following Equation (1), where spreads of the X-ray beam are ignored.

$$f(t)=g(t)/L \quad (1)$$

Figure 3A:
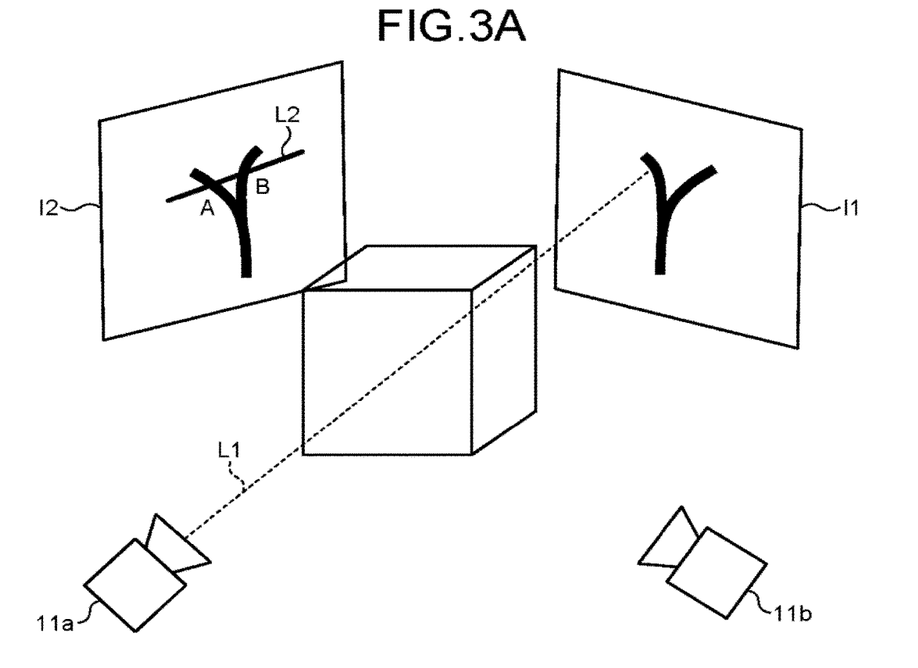
FIG. 3A is a diagram that illustrates the outline of reconstruction by a three-dimensional reconstruction unit according to the first embodiment.
Figure 3B:
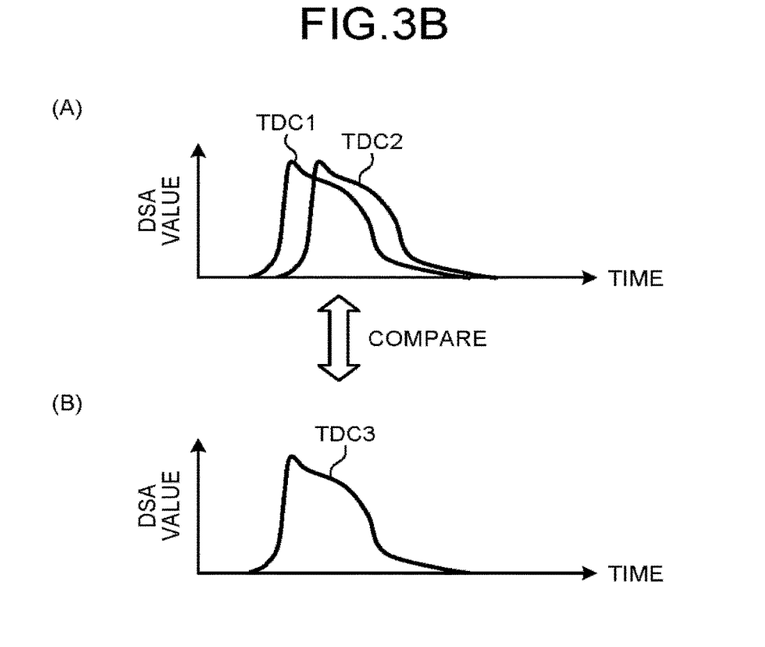
FIG. 3B is a diagram that illustrates the outline of the reconstruction by the three-dimensional reconstruction unit according to the first embodiment.
Figure 4:
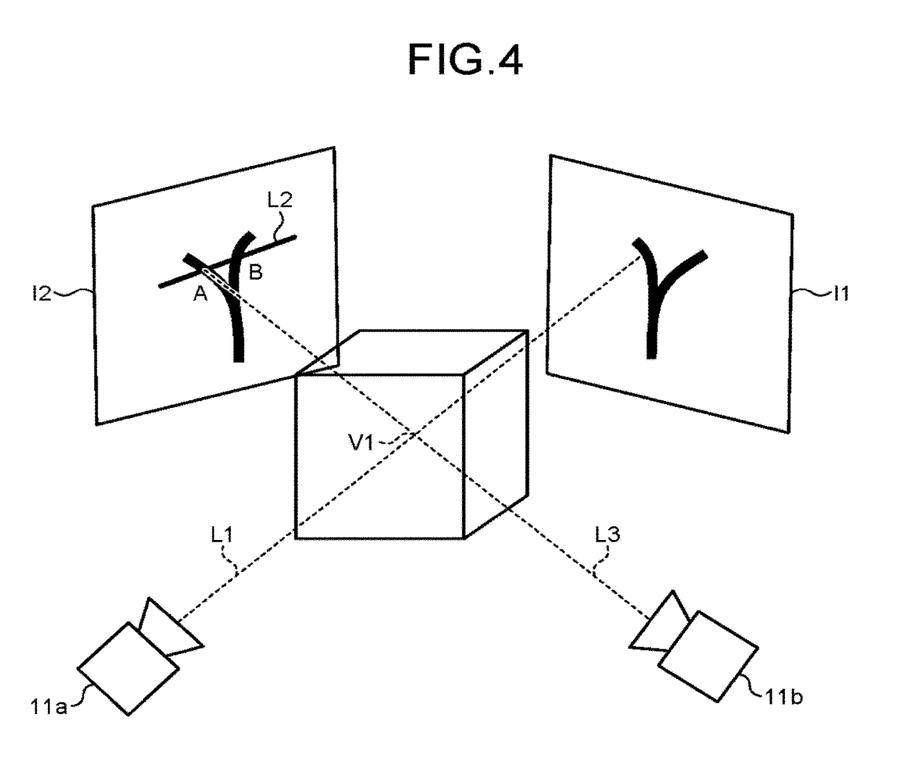
FIG. 4 is a diagram that illustrates the outline of the reconstruction by the three-dimensional reconstruction unit according to the first embodiment.

Furthermore, the obtaining unit 31 sets, as the region of interest, the position (coordinates) that is designated on each of the bi-plane DSA images (Step S106) and identifies a region in the reconstruction space of the region of interest (Step S107). The three-dimensional reconstruction unit 29 reconstructs three-dimensional image data (volume data) by using the moving images that are extracted in two directions (Step S108). Here, an explanation is given, with reference to FIGS. 3A, 3B, and 4, of the outline of a reconstruction by the three-dimensional reconstruction unit 29 according to the first embodiment. FIGS. 3A, 3B, and 4 are diagrams that illustrate the outline of the reconstruction by the three-dimensional reconstruction unit 29 according to the first embodiment.

For example, if volume data is reconstructed from sets of image data in two directions, corresponding positions in the sets of image data are determined. That is, the correspondence position relationship between the blood vessel that is projected onto a DSA image I1 illustrated in FIG. 3A and the blood vessel that is projected onto a DSA image I2 is determined so that the voxel position from which projection is made may be determined, and the volume data may be reconstructed. For example, the object (blood vessel), which is projected onto the intersection point between a straight line L1 that is illustrated in FIG. 3A and the DSA image I1, is located on the straight line L1; however, with only the DSA image I1, it is difficult to determine its position on L1.

Meanwhile, if the straight line L1 is projected onto the DSA image I2, the above-described object (blood vessel) is located at the intersection point between a blood vessel and a line segment L2 that intersects with blood vessels on the DSA image I2 after the straight line L1 is projected. Here, on the DSA image I2, the blood vessels on the line segment L2 are a point A and a point B; therefore, the object (blood vessel), which is projected onto the intersection point between the straight line L1 and the DSA image I1, corresponds to the point A or the point B. Therefore, the three-dimensional reconstruction unit 29 uses the TDC that indicates the blood flow profile to determine the point of the blood vessel that is on the DSA image I2 and that corresponds to the intersection point between the straight line L1 and the DSA image I1, thereby reconstructing volume data.

Specifically, as illustrated in FIG. 3B, the three-dimensional reconstruction unit 29 compares and analyzes a TDC 1 and a TDC 2 that are illustrated in (A) of FIG. 3B and a TDC 3 that is illustrated in (B) of FIG. 3B, thereby determining the corresponding points. Here, the TDC 1 and the TDC 2 indicate the point A and the point B, respectively, on the line segment L2. Moreover, the TDC 3 indicates the intersection point between the straight line L1 and the DSA image I1. For example, as illustrated in FIG. 4, the three-dimensional reconstruction unit 29 determines that the point A is the point that is on the DSA image I2 and that corresponds to the intersection point between the straight line L1 and the DSA image I1. Furthermore, the three-dimensional reconstruction unit 29 determines that an intersection point V1 between the straight line L1 and a straight line L3 is a voxel position from which projection is made, and reconstructs volume data. Here, the straight line L3 is a line connecting the focal point of the X-ray tube 11b and the point A.

As described above, the three-dimensional reconstruction unit 29 uses the blood flow profile of the target blood vessel to determine the correspondence relationship between the blood vessels on the DSA images that are acquired in two directions, thereby reconstructing volume data. Here, the three-dimensional reconstruction unit 29 uses the following Equation (2) as the equation for reconstructing volume data by determining the position relationship between the blood vessels on the DSA images, indicated by the pixel values. Here, "E" in Equation (2) represents a deviation, a vector "g" represents the pixel values on a DSA image that are arranged in a column in order of time, a vector "fr" represents the voxel values of volume data that are also arranged in a column in order of time, and "H" represents a projection matrix for converting a voxel value into a pixel value.

$$E = \|\vec{g} - H\vec{f}z\|^2 \quad (2)$$

Specifically, as represented by Equation (2), the three-dimensional reconstruction unit 29 conducts iterative reconstruction to change the voxel value such that the difference between the value of a pixel included in the region of interest and the pixel value that is derived when the estimated voxel value is projected becomes equal to or less than a predetermined threshold, thereby reconstructing volume data. Here, the three-dimensional reconstruction unit 29 uses the TDC that indicates the blood flow profile as the a priori conditions of the above-described iterative reconstruction. Specifically, the three-dimensional reconstruction unit 29 represents each voxel value with the TDC of the proximal region that is measured by the obtaining unit 31 and conducts iterative reconstruction to change the voxel value by changing the TDC, thereby reconstructing volume data.

Figure 5A:
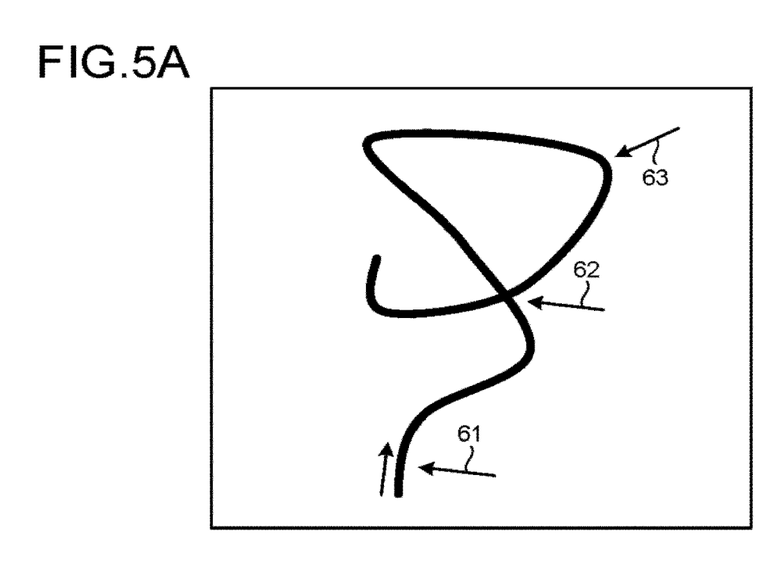
FIGS. 5A to 5D are diagrams that illustrate the relationship between the TDC of a proximal region and the TDC of a distal region according to the first embodiment.

Here, with regard to the TDC of a blood vessel, the relationship between the TDC of the proximal region and the TDC of the distal region is obtained as described below. FIGS. 5A to 5D and FIGS. 6A to 6C are diagrams that illustrate the relationship between the TDC of the proximal region and the TDC of the distal region according to the first embodiment. Here, FIGS. 5A to 5D illustrate a simple model that considers ideal flow, and FIGS. 6A to 6C illustrate a complex model that considers various modulation factors. For example, the blood vessel runs as illustrated in FIG. 5A, and the blood flows upward as indicated by the arrow in the drawing. Furthermore, with the simple model in a case where the position (region) that is designated by an arrow 61 in the drawing is set as the proximal region, the relationship between the TDC of the proximal region and the TDC of the distal region is obtained as in, for example, FIGS. 5B to 5D.

Figure 5B:
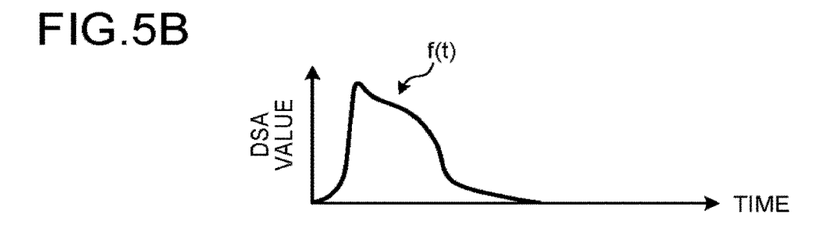
Figure 5C:
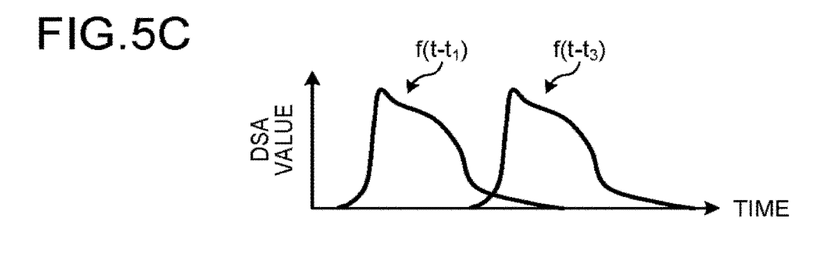
Figure 6A:
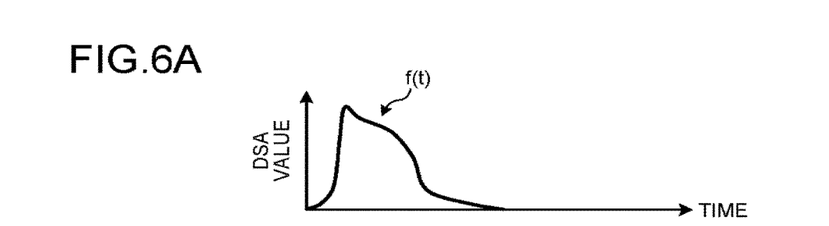
FIGS. 6A to 6C are diagrams that illustrate the relationship between the TDC of the proximal region and the TDC of the distal region according to the first embodiment.
Figure 6B:
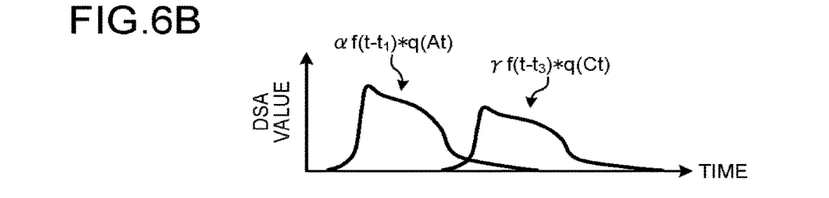
Figure 6C:
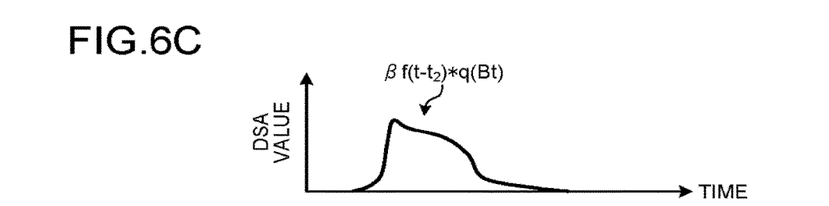

If the entire blood vessel diameter is 1 mm in FIG. 5A and the effect of spreads of the X-ray beam is ignored, the TDC of the proximal region that is designated by the arrow 61, for example, may be represented as TDC "f(t)" whose DSA value rises at time "0" as illustrated in FIG. 5B. Furthermore, in the simple model, the TDC of the distal region that is designated by arrows 62 and 63 may be represented as the TDC that is shifted from TDC "f(t)" with the course of time. Furthermore, for example, as illustrated in FIG. 5C, the TDC of the distal region where the blood vessels are overlapped as designated by the arrow 62 may be represented as TDC "f(t−$t_1$)+f(t−$t_3$)" that is formed by TDC "f(t−$t_1$)" based on the contrast media that passes after time "$t_1$" from the proximal region and TDC "f(t−$t_3$)" based on the contrast media that passes after time "$t_3$" from the proximal region.

Figure 5D:
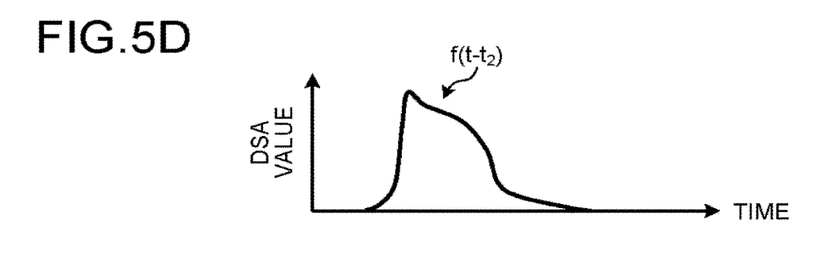

Furthermore, for example, as illustrated in FIG. 5D, the TDC of the distal region where no blood vessels are overlapped as designated by the arrow 63 may be represented as TDC "f(t−$t_2$)" based on the contrast media that passes after time "$t_2$" from the proximal region. Specifically, if it is considered with the simple model, the TDC of the distal region is obtained by simply shifting the reference TDC that is measured in the proximal region in accordance with the time.

However, if the contrast media actually flows through a blood vessel, the contrast media is affected by various modulation factors, such as dilution due to bloods, spread within a blood vessel, speed degradation due to the friction of a blood vessel wall, or reaching delay; therefore, it cannot be said that the simple model illustrated in FIGS. 5A to 5D reflects the actual status. Therefore, according to the present application, the TDC of the proximal region, which serves as a reference, is changed by using the complex model that is illustrated in FIGS. 6A to 6C, and a voxel value is represented by using the changed TDC.

For example, if the complex model is applied to the blood vessel that is illustrated in FIG. 5A, the relationship between the TDC of the proximal region and the TDC of the distal region is obtained as in FIGS. 6A to 6C. For example, as illustrated in FIG. 6A, the TDC of the proximal region that is designated by the arrow 61 may be represented as TDC "f(t)" whose DSA value rises from the time "0" in the same manner as in FIG. 5B. Furthermore, in the complex model, the TDC of the distal region that is designated by the arrows 62 and 63 is represented as the TDC that is obtained by deforming the TDC. Shift from TDC "f(t)" is applied with same manner with the simple model. The deformation is mainly composed of two factors, one is weakening/strengthening due to dilution of the contrast media, the thickness change of a blood vessel or the like, and another is spread of the contrast media caused by the Brownian motion, the friction of a blood vessel wall or the like. The weakening/strengthening can be represented by "α" to "γ". The spread is represented by "q(At)" to "q(Ct)".

Furthermore, for example, as illustrated in FIG. 6B, the TDC of the distal region where the blood vessels are overlapped as designated by the arrow 62 may be represented as TDC "αf(t−$t_1$)*q(At)+γf(t−$t_3$)*q(Ct)" that is formed by using TDC "αf(t−$t_1$)*q(At)" and TDC "γf(t−$t_3$)*q(Ct)". Here, the TDC "αf(t−$t_1$)*q(At)" is obtained by deforming TDC "f(t−$t_1$)" based on the contrast media that passes after the time "$t_1$" from the proximal region with "a" and "q(At)". Moreover, the TDC "γf(t−$t_3$)*q(Ct)" is obtained by deforming TDC "f(t−$t_3$)" based on the contrast media that passes after the time "$t_3$" from the proximal region with "γ" and "q(Ct)".

Furthermore, for example, as illustrated in FIG. 6C, the TDC of the distal region where no blood vessels are overlapped as designated by the arrow 63 may be represented as TDC "βf(t−$t_2$)*q(Bt)" that is obtained by deforming TDC "f(t−$t_2$)" based on the contrast media that passes after the time "$t_2$" from the proximal region with "β" and "q(Bt)". The three-dimensional reconstruction unit 29 according to the first embodiment uses the above-described complex model to estimate a voxel value.

For example, the three-dimensional reconstruction unit 29 uses the following Equation (3) to calculate the voxel value that is each element of a vector "$f_r$". Here, "$f_r$" in Equation (3) represents a voxel value, "A" represents the factor for adjusting dilution of the contrast media and the beam hardening effect, and "Δt" represents the speed degradation due to the friction of a blood vessel wall and the reaching delay time. Furthermore, "q(t)" in Equation (3) represents spread, and "*" represents a convolution operator.

$$f_r = Aq(t) * f(t-\Delta t) \quad (3)$$

For example, the three-dimensional reconstruction unit 29 obtains, as a voxel value, the TDC that is obtained by deforming "f(t)" with various modulation factors as represented by Equation (3). Here, the spread "q(t)" in Equation (3) is calculated by using the following Equation (4). Here, "σ" in Equation (4) represents a spread coefficient.

$$q(t) = \frac{1}{\sqrt{2\pi\sigma^2}} \exp\left(\frac{t^2}{2\sigma^2}\right) \quad (4)$$

Furthermore, in the above-described Equation (4), although spread is represented by using an ideal equation, it sometimes actually deviates from the ideal equation due to the effect of friction of a blood vessel wall, or the like. Therefore, in such a case, the three-dimensional reconstruction unit 29 compares the TDCs of the distal region and the proximal region where no blood vessels are overlapped, calculates the spread "q(t)" on the basis of changes in the two TDCs. Furthermore, the three-dimensional reconstruction unit 29 performs the above-described operation by using the calculated spread "q(t)".

Furthermore, if the region (the region of interest) to be reconstructed is located close to the proximal region and it is the extremely limited region, it is considered that there is hardly any effect of spread; therefore, the three-dimensional reconstruction unit 29 represents a voxel value by using the following Equation (5) that is a simplified form of Equation (3).

$$f_r = Af(t-\Delta t) \quad (5)$$

As described above, the three-dimensional reconstruction unit 29 changes each voxel value in volume data by using Equation (3) or Equation (5) and conducts iterative reconstruction so as to reduce the deviation between the value that is obtained by projecting the changed voxel value and the actually acquired pixel value of the DSA image. That is, the three-dimensional reconstruction unit 29 changes a voxel value by using "A", "q(t)", or the like, so as to reduce the deviation from the pixel value of the DSA image that is acquired by the first acquisition mechanism and the deviation from the pixel value of the DSA image that is acquired by the second acquisition mechanism.

Then, if the deviation from the pixel value on the DSA image that is acquired by the first acquisition mechanism and the deviation from the pixel value on the DSA image that is acquired by the second acquisition mechanism are equal to or less than a predetermined threshold, the three-dimensional reconstruction unit 29 terminates the reconstruction operation and stores the reconstructed volume data in the image memory 22. Furthermore, during the reconstruction operation by the three-dimensional reconstruction unit 29, it may be determined whether the deviation is reduced by minutely changing each undetermined value (A, Δt, or the like) for each voxel; however, the undetermined value may be changed such that back projection is conducted on the obtained deviation and Equation (3) or Equation (5) is fitted into the sum of the back projection result and the previously estimated voxel value. Thus, the processing time may be shortened.

With reference back to FIG. 2, after the reconstruction of volume data is executed as described above (Step S108), the three-dimensional image processing unit 25 reads the volume data from the image memory 22 and generates a blood vessel image from the read volume data (Step S109). Then, the display control unit 32 causes the display unit 40 to display a three-dimensional roadmap image where the generated blood vessel image is superimposed on the fluoroscopic image that is run in real time (Step S110).

Figure 7:
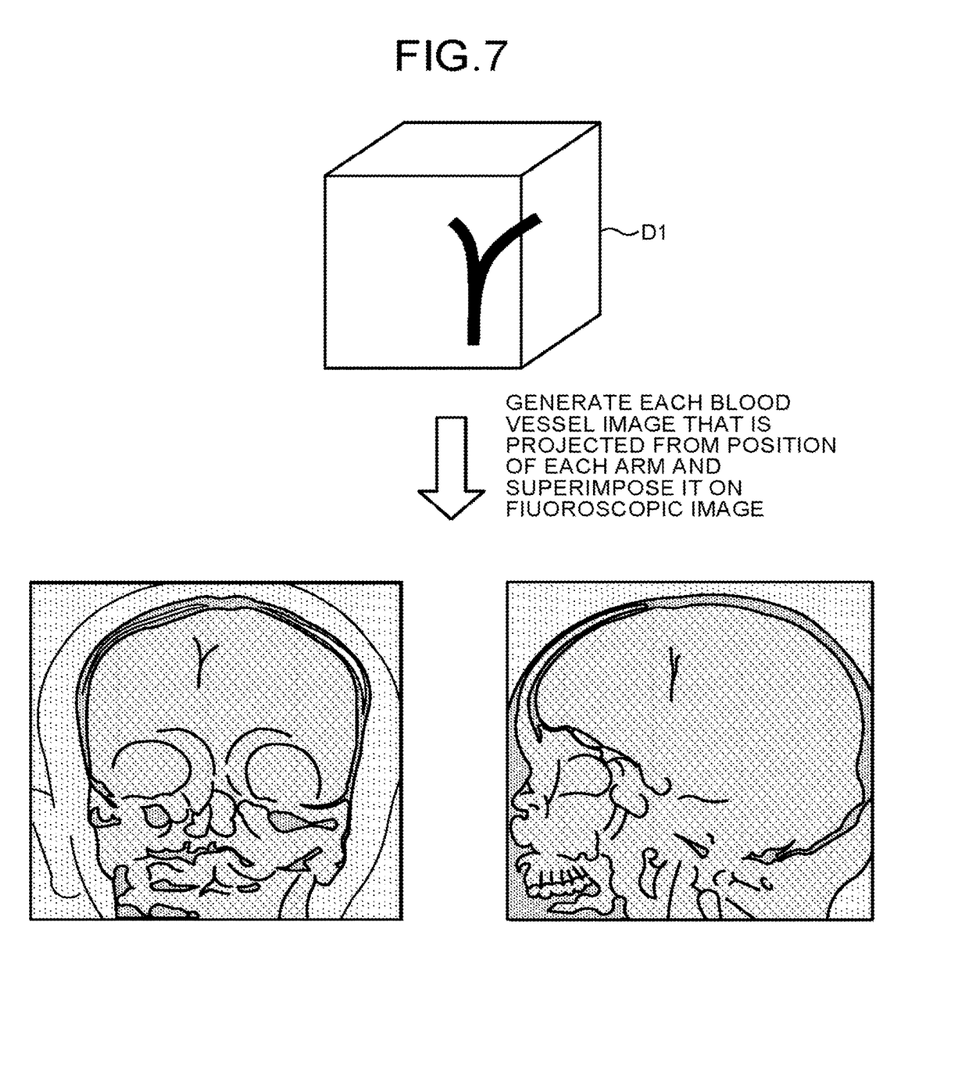
FIG. 7 is a diagram that illustrates an example of a three-dimensional roadmap image that is displayed by a display control unit according to the first embodiment.

FIG. 7 is a diagram that illustrates an example of the three-dimensional roadmap image that is displayed by the display control unit 32 according to the first embodiment. For example, as illustrated in FIG. 7, the three-dimensional image processing unit 25 uses volume data D1 that is reconstructed by the three-dimensional reconstruction unit 29 to generate a blood vessel image that is projected from the position of each arm at the present moment, and it causes the display unit 40 to display a three-dimensional roadmap image where each of them is superimposed on the fluoroscopic image that is acquired by the bi-plane. Here, the three-dimensional image processing unit 25 generates, as the blood vessel image, a volume rendering image, a projection image, an MIP image, or the like.

In the above-described embodiment, an explanation is given of a case where the reconstruction is conducted such that the deviation between the pixel value and the value that is obtained by projecting the estimated voxel value is reduced. However, this is not a limitation on the embodiment and, for example, there may be a case where the information on an adjacent voxel value is used. Specifically, in some cases, with regard to adjacent voxels, various modulation factors almost match. Therefore, the three-dimensional reconstruction unit 29 may perform reconstruction so as to minimize the difference between the voxel values of adjacent voxels as well as to reduce the deviation between the pixel value and the value that is obtained by projecting the estimated voxel value.

Furthermore, in the X-ray diagnostic apparatus 1 according to the first embodiment, the reconstruction may be conducted by using the time change of the pixel values of a time-course DSA image. In such a case, the obtaining unit 31 acquires the information on the time change of the contrast media on a pixel by pixel basis with regard to each of the groups of time-course X-ray images. The three-dimensional reconstruction unit 29 reconstructs three-dimensional image data by using the sum of time changes.

Here, the three-dimensional reconstruction unit 29 reconstructs continuous three-dimensional image data such that the time change of the voxel value is continuous with regard to the voxel at the identical position in the three-dimensional image data that is continuous in terms of time. Furthermore, with regard to the voxel at the identical position in the three-dimensional image data that is continuous in terms of time, the three-dimensional reconstruction unit 29 reconstructs, as a blood vessel region, the voxel of which the time change in the voxel value is negative.

Modified Example 1

In the above-described embodiment, an explanation is given of a case where a three-dimensional roadmap image is generated and displayed by using reconstructed volume data. However, this is not a limitation on the embodiment and, for example, there may be a case where the angle that is appropriate for performing a surgery is provided. For example, during intervention or angiographic examination, the display control unit 32 first causes the display unit 40 to display a blood-vessel volume rendering image that is obtained when volume rendering processing is performed on the reconstructed volume data based on the angle of the arm at the present moment. Here, if an operator changes the orientation of a blood vessel via the input unit, the display control unit 32 causes the display unit 40 to display the change information on the arm angle in accordance with the change in the orientation of the blood vessel. For example, if an operator changes the orientation of a blood vessel in the volume rendering image so as to easily see the bifurcation of the blood vessel, the display control unit 32 causes the display unit 40 to display the information on the arm angle with which the blood vessel in the changed orientation is extracted on the fluoroscopic image. If the operator moves the arm to obtain the displayed angle, the target blood vessel is extracted on the fluoroscopic image at an easily viewable angle.

As described above, according to the first embodiment, with regard to each of the groups of time-course X-ray images that are obtained by acquiring the subject, into which the contrast media is injected, in at least two directions, the obtaining unit 31 acquires the value of a pixel that is included in the region of interest and the first transition information that indicates the transition of the signal intensity of the contrast media in the region to which the contrast media flows earlier than the region of interest. The three-dimensional reconstruction unit 29 reconstructs three-dimensional image data such that the value that is obtained by projecting the voxel value, which is represented by the second transition information that is obtained by deforming the first transition information with the factor that is related to the contrast media, approximates the value of a corresponding pixel in each of the groups of time-course X-ray images. Therefore, with the X-ray diagnostic apparatus 1 according to the first embodiment, three-dimensional image data may be easily reconstructed from a DSA image that is acquired by the bi-plane, and image data for a three-dimensional roadmap image may be acquired in a short time without significantly deviating from the usual surgery.

Furthermore, according to the first embodiment, the three-dimensional reconstruction unit 29 reconstructs three-dimensional image data such that the value that is obtained by projecting the voxel value approximates the pixel value, the voxel value being represented by the second transition information that is changed with at least one factor among dilution and spread of the contrast media within a blood vessel, speed degradation due to the friction of a blood vessel wall, and a reaching delay time. Therefore, the X-ray diagnostic apparatus 1 according to the first embodiment may conduct reconstruction in consideration of the contrast media that actually flows through a blood vessel.

Furthermore, according to the first embodiment, the three-dimensional reconstruction unit 29 reconstructs three-dimensional image data such that the difference in the voxel values of adjacent voxels is minimized. Thus, the X-ray diagnostic apparatus 1 according to the first embodiment may perform reconstruction with a higher accuracy.

Second Embodiment

Furthermore, although the first embodiment has been described above, various different embodiments may be implemented other than the above-described first embodiment.

Components of each apparatus illustrated according to the first embodiment are functionally conceptual and do not necessarily need to be physically configured as illustrated in the drawings. Specifically, specific forms of separation and combination of each apparatus are not limited to those depicted in the drawings, and a configuration may be such that all or some of them are functionally or physically separated or combined in an arbitrary unit depending on various types of loads or usages. Moreover, all or any of the various processing functions that are performed by each apparatus may be implemented by a CPU and a program that is analyzed and executed by the CPU or may be implemented as wired logic hardware.

Furthermore, the control method that is described according to the first embodiment may be implemented if a prepared control program is performed by a computer, such as a personal computer or workstation. The control program may be distributed via a network, such as the Internet. Moreover, the control program may be recorded in a recording medium readable by a computer, such as a hard disk, flexible disk (FD), CD-ROM, MO, or DVD, and it may be read from the recording medium by the computer so as to be executed.

As described above, according to the first embodiment and the second embodiment, the X-ray diagnostic apparatus according to the present embodiment may easily reconstruct three-dimensional image data from the DSA image that is acquired by the bi-plane.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
processing circuitry configured to
obtain, with respect to a plurality of groups of time-course fluoroscopic images that are obtained by acquiring a subject injected with a contrast media, in at least two directions, each of which intersect, a first time density curve that indicates transition of a signal intensity of the contrast media in a proximal region to which the contrast media flows earlier than a region of interest, and
reconstruct three-dimensional image data in the region of interest such that a value that is obtained by projecting a voxel value approximates a value of a corresponding pixel in each of the groups of time-course fluoroscopic images, the voxel value being represented by a second time density curve that is obtained by deforming the first time density curve with a factor that is related to the contrast media; and
a display configured to display a newly obtained fluoroscopic image with a blood vessel image based on the three-dimensional image data.

2. The X-ray diagnostic apparatus according to claim 1, wherein the display is configured to display a superimposed image obtained by superimposing the blood vessel image on the newly obtained fluoroscopic image.

3. The X-ray diagnostic apparatus according to claim 1, wherein the processing circuitry is configured to reconstruct the three-dimensional image data such that the value that is obtained by projecting the voxel value approximates the value of the pixel, the voxel value being represented by using the second time density curve that is changed with at least one factor among dilution and spread of the contrast media within a blood vessel, speed degradation due to a friction of a blood vessel wall, and a reaching delay time.

4. The X-ray diagnostic apparatus according to claim 1, wherein the processing circuitry is configured to obtain each of the first time density curve in the proximal region designated by an operator for each fluoroscopic image that has been acquired in the two directions by bi-plane system.

5. The X-ray diagnostic apparatus according to claim 1, wherein the region of interest includes a region where a blood vessel is bifurcated.

6. The X-ray diagnostic apparatus according to claim 1, wherein the display is configured to display the blood vessel image corresponding to a direction of acquiring the newly obtained fluoroscopic image.

7. The X-ray diagnostic apparatus according to claim 3, wherein the processing circuitry is configured to reconstruct the three-dimensional image data such that a difference in voxel values of adjacent voxels is minimized.

8. The X-ray diagnostic apparatus according to claim 1, wherein the processing circuitry is configured to
obtain information on a time change in the contrast media of each pixel with regard to each of the groups of time-course fluoroscopic images, and
reconstruct the three-dimensional image data by using a sum of the time changes.

9. The X-ray diagnostic apparatus according to claim 8, wherein the processing circuitry is configured to reconstruct the three-dimensional image data such that a time change in a voxel value is continuous with respect to a voxel at an identical position in three-dimensional image data that is continuous in terms of time.

10. The X-ray diagnostic apparatus according to claim 8, wherein the processing circuitry is configured to reconstruct, as a blood vessel region, a voxel of which a time change in a voxel value is negative with respect to a voxel at an identical position in three-dimensional image data that is continuous in terms of time.

* * * * *